United States Patent
Gerald, II et al.

(10) Patent No.: US 7,268,552 B1
(45) Date of Patent: *Sep. 11, 2007

(54) CAPILLARY TOROID CAVITY DETECTOR FOR HIGH PRESSURE NMR

(75) Inventors: Rex E. Gerald, II, Brookfield, IL (US); Michael J. Chen, Downers Grove, IL (US); Robert J. Klingler, Glenview, IL (US); Jerome W. Rathke, Honer Glen, IL (US); Marc ter Horst, Chapel Hill, NC (US)

(73) Assignee: United States of America as represented by the United States Department of Energy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/158,302

(22) Filed: Jun. 21, 2005

Related U.S. Application Data

(60) Provisional application No. 60/581,561, filed on Jun. 21, 2004.

(51) Int. Cl.
*G01V 3/00* (2006.01)
(52) U.S. Cl. .................. 324/318; 324/321; 324/306; 324/303
(58) Field of Classification Search .................. None
See application file for complete search history.

(56) References Cited

U.S. PATENT DOCUMENTS

| | | | | |
|---|---|---|---|---|
| 5,574,370 | A * | 11/1996 | Woelk et al. | 324/320 |
| 6,046,592 | A * | 4/2000 | Rathke et al. | 324/321 |
| 6,191,583 | B1 * | 2/2001 | Gerald et al. | 324/321 |
| 6,538,444 | B2 * | 3/2003 | Gerald et al. | 324/318 |
| 6,575,969 | B1 * | 6/2003 | Rittman et al. | 606/41 |
| 6,720,769 | B2 * | 4/2004 | Gerald et al. | 324/318 |
| 6,727,696 | B2 * | 4/2004 | Kruspe et al. | 324/303 |
| 6,822,454 | B2 * | 11/2004 | Peck et al. | 324/321 |
| 6,896,675 | B2 * | 5/2005 | Leung et al. | 606/49 |
| 2002/0149369 | A1 * | 10/2002 | Peck et al. | 324/321 |
| 2002/0153888 | A1 * | 10/2002 | Kruspe et al. | 324/303 |
| 2005/0030033 | A1 * | 2/2005 | Peck et al. | 324/321 |
| 2005/0253587 | A1 * | 11/2005 | Peck et al. | 324/321 |

* cited by examiner

*Primary Examiner*—Brij Shrivastav
*Assistant Examiner*—Tiffany A. Fetzner
(74) *Attorney, Agent, or Firm*—Mark F. LaMarre; Mark P. Dvorscak; Paul A. Gottlieb

(57) ABSTRACT

A Toroid Cavity Detector (TCD) is provided for implementing nuclear magnetic resonance (NMR) studies of chemical reactions under conditions of high pressures and temperatures. A toroid cavity contains an elongated central conductor extending within the toroid cavity. The toroid cavity and central conductor generate an RF magnetic field for NMR analysis. A flow-through capillary sample container is located within the toroid cavity adjacent to the central conductor to subject a sample material flowing through the capillary to a static magnetic field and to enable NMR spectra to be recorded of the material in the capillary under a temperature and high pressure environment.

24 Claims, 8 Drawing Sheets

CAPILLARY TOROID CAVITY DETECTOR FOR HIGH PRESSURE NMR

This application claim priority from Provisional Application No. 60/581,561 filed on Jun. 21, 2004.

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to a combination of the Toroid Cavity Detector (TCD) with a flow-through capillary sample chamber for implementing nuclear magnetic resonance (NMR) studies of chemical reactions under conditions of high pressures and temperatures.

DESCRIPTION OF THE RELATED ART

Nuclear magnetic resonance (NMR) analysis is a powerful method by which to determine chemical structures and to examine reaction dynamics in a diversity of chemical and biochemical systems.

For example, U.S. Pat. No. 5,574,370, issued Nov. 12, 1996 to Woelk et al., discloses a toroid cavity detection (TCD) system for determining the spectral properties and distances from a fixed line for a sample using Nuclear Magnetic Resonance. The detection system consists of a toroid with a central conductor oriented along the main axis of the toroidal cylinder and parallel to a static uniform magnetic field, $B_0$. An RF signal is inputted to the central conductor to produce a magnetic field $B_1$ perpendicular to the central axis of the toroid and whose field strength varies as the inverse of the radial position within the toroid. The toroid cavity detection system can be used to encapsulate a sample, or the detection system can be perforated to allow a sample to flow into the detection device or to place the samples in specified sample tubes. The central conductor can also be coated to determine the spectral properties of the coating and the coating thickness. The sample is then subjected to the respective magnetic fields and the responses measured to determine the desired properties.

U.S. Pat. No. 6,046,592, issued Apr. 4, 2000 to Rathke et al., discloses a near-electrode imager for employing nuclear magnetic resonance imaging to provide in situ measurements of electrochemical properties of a sample as a function of distance from a working electrode. The near-electrode imager uses the radio frequency magnetic field gradient within a cylindrical toroid cavity resonator to provide high-resolution nuclear magnetic resonance spectral information on electrolyte materials.

U.S. Pat. No. 6,191,583, issued Feb. 20, 2001 to Gerald II, discloses a toroid cavity detector that includes an outer cylindrical housing through which extends a wire along the central axis of the cylindrical housing from a closed bottom portion to the closed top end of the cylindrical housing. In order to analyze a sample placed in the housing, the housing is placed in an eternally applied static main homogeneous magnetic field ($B_0$). An RF current pulse is supplied through the wire such that an alternately energized and de-energized magnetic field ($B_1$) is produced in the toroid cavity. The field $B_1$ is oriented perpendicular to the field $B_0$. Following the RF current pulse, the response of the sample to the applied field $B_0$ is detected and analyzed. In order to minimize the detrimental effect of probe ringing, the cylindrically shaped housing is elongated sufficiently in length so that the top and bottom portions are located in weaker, fringe areas of the static main magnetic field $B_0$. In addition, a material that tends to lessen the effect of probe ringing is positioned along the top and bottom ends of the toroid cavity. In another embodiment, a plug is positioned adjacent to the inside of the top and bottom ends of the toroid cavity so that the sample contained in the toroid cavity is maintained in the strongest and most homogeneous region of the static magnetic field $B_0$.

U.S. Pat. No. 6,538,444, issued Mar. 25, 2003 to Gerald II et al., discloses a two dimensional $B_1$-gradient NMR imager and methods for non-invasive spectroscopic investigations and imaging of the internal distribution and speciation of materials of fluid, solid, and semisolid objects in two spatial dimensions utilizing a toroid cavity detector. An RF signal transmitter/receiver generates a magnetic field $B_1$ within the toroid cavity and receives a sample response to the magnetic fields $B_0$ and $B_1$. A pivot angle position controller adjusts a pivot angle position of the toroid cavity and enclosed sample to vary an angle between the magnetic field $B_0$ and the central axis of the toroid cavity. A positional rotation controller positions the toroid cavity and enclosed sample at variable angular orientations relative to an initial position and a plane formed by the externally applied static main magnetic field $B_0$ and the central axis of the toroid cavity. A computer sequentially receives and processes sample responses to produce a two-dimensional image.

U.S. Pat. No. 6,720,769, issued Apr. 13, 2004 to Gerald II et al., discloses a detecting method and detector that expands the capabilities of Nuclear Magnetic Resonance (NMR) analysis. A Rotational Exchange Gradient Imager (REGI) allows for real-time, in situ investigation of materials subjected to the effects of centrifugal force by NMR analysis. The REGI comprises a cylindrical stator formed of an electrically conductive, non-magnetic material, a rotor contained in the cylindrical stator formed of an electrically non-conductive, non-magnetic material, and a conductor located along a central axis of the cylindrical stator. A sample is contained within the rotor. The stator and central conductor serve to generate the RF magnetic field for NMR analysis. The rotor containing the sample is rotated within a stable air bearing formed between the cylindrical stator and rotor.

The subject matter of each of the U.S. Pat. Nos. 5,574,370, 6,046,592, 6,191,583, 6,538,444, and 6,720,769 is incorporated herein by reference.

There is a need in the art for a device that can measure NMR spectra of sample solutions at high temperatures and pressures. A Toroid Cavity Detector (TCD) is the simplest and most used device for recording high resolution NMR spectra under conditions of high pressure and temperatures, particularly of solutes dissolved in supercritical $CO_2$. However, the TCD is not widely used in the NMR community because high-pressure NMR probes are not commercially available, and there are other devices that are easier to use. However, the other devices cannot operate in the high temperature and pressure range of the TCD.

The existing high-pressure NMR probes are specialized devices used in a small number of laboratories primarily in the United States and Europe. Recently reported NMR sample tubes designed for high-pressure experiments can be used; however, they are fabricated from plastics that are not compatible with many solvents and high temperatures.

The toroid cavity detector (TCD) has been developed for the purpose of conducting nuclear magnetic resonance spectroscopy (NMR) experiments under conditions of high pressure and temperature. The general design of a TCD comprises a cylindrical high-pressure metal vessel with one threaded open end, a metal central conductor, a high-pressure screw cap, and high-pressure ports fitted with machined ferrule seats. The high-pressure ports are typically integrated into the screw cap, but can also be added to the base of the metal vessel. The sample capacity in a typical TCD is 8 cm$^3$. The TCDs are fabricated from a beryllium-copper alloy. Typical operating conditions cover the pressure range 0–600 atm, and temperature range –10–150° C. The TCD is the simplest and most used device for recording high-resolution NMR spectra of solutes dissolved in supercritical $CO_2$. The TCD is not widely used in the NMR spectroscopy community because it is not generally commercially available.

Three other known devices (high-pressure sample containers) may offer greater simplicity of use. However, these devices must be operated under significantly lower pressures and temperatures, and some can fail with catastrophic results. In addition, the TCD is an integral part of an NMR probe whereas these other devices are simply sample containers, which must be inserted into a commercially available NMR probe. The advantage of these known devices, the capillary tube, sapphire, and PEEK (poly ether ether ketone) high-pressure sample containers is that they are easy to use. The capillary tube device has the additional advantages of commercial availability. The use of a capillary tube as a high-pressure sample container has the advantage of enhanced safety because the sample volume per unit length is very small. The sapphire and PEEK tubes require careful fabrication or machining of the main cylindrical container, and a secure attachment of the valve assembly at one end. (The sapphire tubes are single crystals pulled from a melt.) One also must consider the $^{13}C$ background signal from the PEEK plastic. Wallen, et al. have reported a broad component in the $^{13}C$ NMR spectrum that they attribute to PEEK plastic. The acquisition of the FID was delayed by 120 µs to eliminate the background signal. While this approach can be used, it can require significant first-order phase corrections. Another serious concern for using plastic sample cells is the compatibility of the cell with the solvent or solute under study. Even in the case of low swelling or low reactivity of the solvent with the cell, it becomes necessary to test the cell prior to each use to assure safe operation.

In one example, a one-piece high-pressure sample container fabricated from the PEEK plastic included an integrated valve. A drawback of the capillary tube system is the small total sample volume, which results in poor sensitivity. Yonkers, et al. improved the sensitivity of the capillary tube system by folding the capillary tube in a zigzag pattern. The drawback of this approach is that there is a 40% failure rate for these tubes due to the sharp bends. In addition, to maximize sensitivity by this approach all the capillary bends must be parallel to the direction of the magnetic field otherwise susceptibility mismatch will degrade the NMR line shape.

A principal object of the present invention is to provide a combination of the Toroid Cavity Detector (TCD) with a flow-through capillary sample chamber for implementing NMR studies of chemical reactions under conditions of high pressures and temperatures.

Other important objects of the present invention are to provide such combination of the Toroid Cavity Detector (TCD) with a flow-through capillary sample chamber that is a simple, inexpensive and safe device.

Other important objects of the present invention are to provide such combination of the Toroid Cavity Detector (TCD) with a flow-through capillary sample chamber substantially without negative effect and that overcomes some disadvantages of prior art arrangements.

SUMMARY OF THE INVENTION

In brief, a Toroid Cavity Detector (TCD) for implementing nuclear magnetic resonance (NMR) studies of chemical reactions under conditions of high pressures and temperatures is provided. A toroid cavity contains an elongated central conductor extending within the toroid cavity. The toroid cavity and central conductor generate an RF magnetic field for NMR analysis. A flow-through capillary sample container is located within the toroid cavity having at least a portion adjacent to the central conductor to subject a sample material flowing through the capillary to a static magnetic field and to enable NMR spectra to be recorded of the material in the capillary under a high temperature and high pressure environment.

In accordance with features of the invention, the capillary sample container can include a plurality of capillary loops, each loop including a portion located adjacent to the central conductor. Also, the capillary sample container can be wound around the central conductor. The elongated central conductor extending within the toroid cavity can include an offset portion located adjacent to a predefined portion of the capillary sample container to provide reduced line shape distortion. The elongated central conductor extending within the toroid cavity can include a side entrance into the toroid cavity to selectively interrogate only that section of the capillary sample container that is spaced apart from the top and bottom of the toroid cavity. The toroid cavity detector is formed by a metal container, for example, copper, and provides a secondary safety function in the event of a failure of the capillary sample container.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1A:
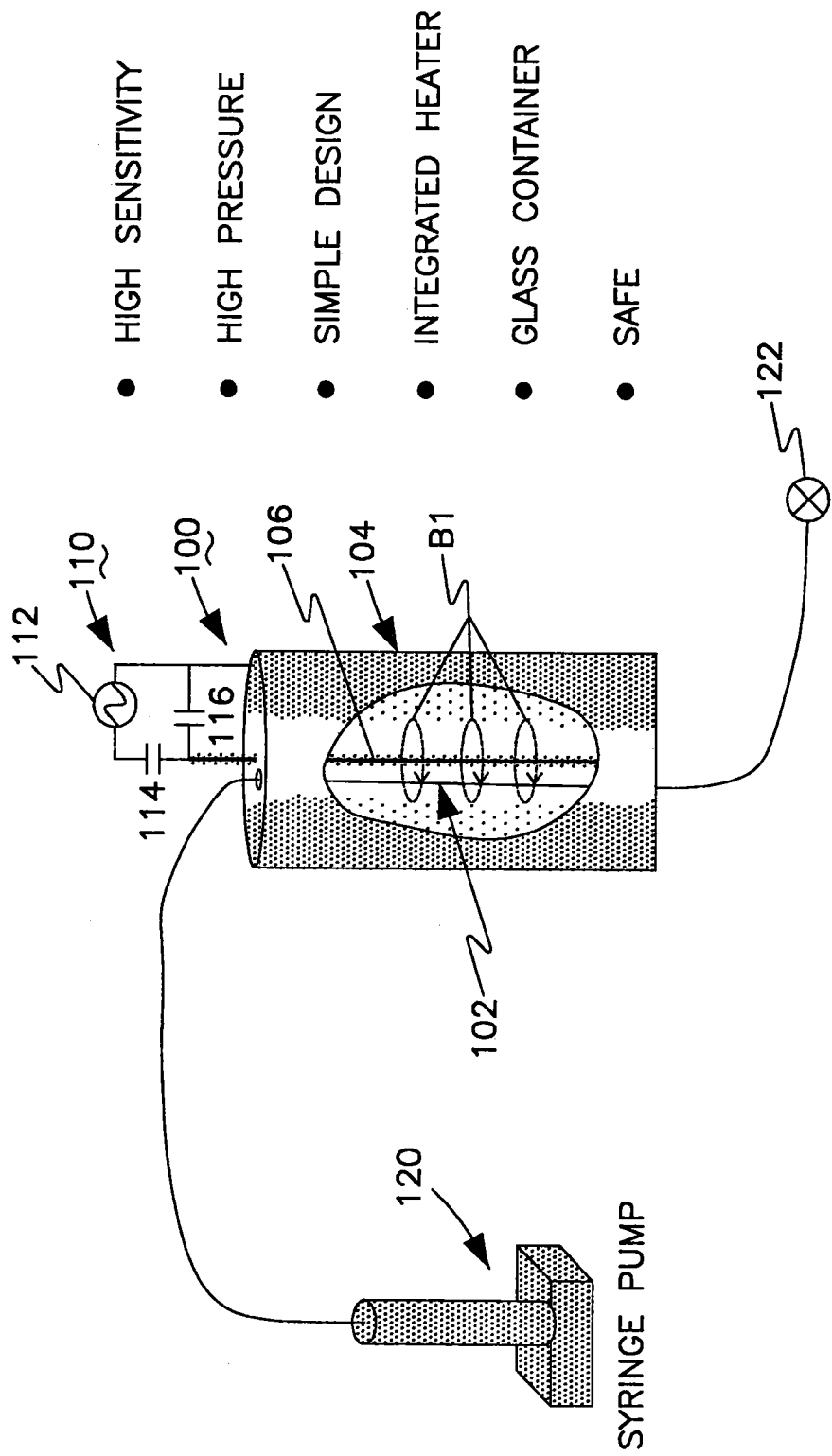
FIG. 1A illustrates a first embodiment of a high-pressure capillary TCD of a preferred embodiment.

In accordance with features of the invention, a capillary TCD of the invention is a simple, inexpensive, and safe device that will allow a broad range of users, particularly in industry, to perform NMR studies of chemical interactions/reactions under conditions of high pressures and high temperatures. Herein, high pressure refers to a pressure from about 5 atmospheres (atm) to about 1500 atm (1.5 kilobars) and preferably a pressure from about 70 atm to about 250 atm. Further, herein high temperatures refer to a temperature range of about 50° C. to about 500° C. and preferably from about 100° C. to about 250° C. With suitable modification, the device of this invention may be used at low temperatures in the range from about −200° C. to about 0° C. and preferably within the range from −100° C. to 0° C. The device may also be used in the range from 0° C. to about 50° C. In addition, for standard NMR analyses under ambient conditions, the capillary TCD probe offers high sample throughput by employing a sample flow through design. The safety and ease of operation are key issues considered by scientific staff at chemical companies when selecting specialized NMR probes. The capillary TCD was designed for use by a technician. The capillary TCD of the present invention is particularly useful to the chemical industry because it can be used to study chemical reactions in supercritical $CO_2$, a green solvent.

The present invention combines the attractive features of a capillary sample container and the sensitivity of a TCD. The development of the capillary TCD for NMR analyses of mass-limited biological samples is currently motivated by the promise of a substantial increase in sensitivity. However, the inhomogeneity of the external magnetic field ($B_0$) over the sample volume in a TCD is a problem that results in reduced sensitivity. High pressure and high temperature capillary tubing can be use with the device of this invention. High pressure capillary tubing of this type has an inside diameter from about 1.0 micrometer (μm) to about 2.0 millimeters (mm) and preferably from about 50 μm to about 200 μm. The wall thickness of suitable high pressure tubing is from 10 μm to 1 millimeter and preferably from about 10 μm to about 200 μm. The capillary tubing is preferably made from a non-electrically conductive material such as, but not limited to, glass, quartz, high performance polymers (i.e., PEEK, PTFE, and poly imides), metal oxides and ceramics. Difficulties with high pressure and high temperature NMR analysis are due to the size of the sample. With the use of micro volumes of samples NMR analysis at these extreme conditions is safely attainable.

In accordance with features of the present invention, improved $B_0$ homogeneity in TCD NMR probes is provided while taking advantage of a continuous column of sample. In the capillary TCD of the invention, there are substantially no susceptibility mismatches due to abrupt interfaces, as in the case of a conventional TCD. One embodiment of a capillary TCD of the invention that employs a straight capillary tube mounted next to the central conductor was tested to 350 atm (5000 psi) and exhibited good NMR sensitivity.

The geometrical interface between two materials with dissimilar volume magnetic susceptibilities is generally known to cause magnetic field distortions in the NMR-active space. In TCDs the magnetic field distortion problem is due to the exterior and interior interfaces of the cylindrical toroid cavity. An exterior air-copper interface at the top and bottom of the toroid cavity causes distortions in the magnetic field that can be substantially eliminated by elongating the cavity. An interior copper-sample interface at the top and bottom of the toroid cavity also causes distortions in the magnetic field in the sample volume, but elongating the cavity cannot eliminate these distortions.

In accordance with features of the invention, a continuous capillary sample container eliminates magnetic field distortions caused by the interior interfaces at the top and bottom of the toroid cavity. This is a passive shimming approach to the susceptibility mismatch problem that takes advantage of materials with identical volume susceptibilities and geometrical forms to homogenize the magnetic field in the sensitive region of the NMR probe. The use of a continuous column of sample takes advantage of the commonly used approach to homogenize magnetic fields, the active shimming method. Active shimming requires energized magnet coils that generate correction magnetic fields. The magnet coils that are included in commercial NMR instruments were designed to homogenize the sample volume in commercial Helmholtz-style NMR probes, and are not capable of correcting all magnetic field distortions caused by TCD probes. Therefore, magnet coils specifically designed for TCD probes are highly desirable, but not available on commercial instruments. A combination of the continuous capillary tube and standard active shimming methods provides enhanced magnetic field homogeneity performance of capillary TCD probes of the preferred embodiment.

Having reference now to the drawings, FIG. 1A illustrates a first embodiment of a high-pressure capillary Toroid Cavity Detector (TCD) of the preferred embodiment generally designated by the reference character 100. High-pressure capillary TCD 100 includes a flow-through tube or flow-through capillary sample container 102 located within a toroid cavity 104 to subject a sample material flowing through the capillary sample container to a magnetic field and to enable NMR spectra to be recorded of the material in the capillary under a high temperature and pressure environment of the TCD 100. The flow-through capillary sample container 102 is located proximate to a non-coiled elongated central conductor 106 extending along a predefined axis, such as a central axis of the toroid cavity 104.

A TCD RF circuit generally designated by the reference character 110 generates an RF signal that is inputted to the central conductor 106 from an RF source 112 via a matching capacitor Cm 114 with a tuning capacitor Ct 116 connected between the junction of matching capacitor Cm and the central conductor 106 and the toroid cavity 104. RF signal applied to the central conductor 106 produces a magnetic field $B_1$ perpendicular to the central axis of the toroid cavity 104 indicated by arrows labeled B1. The produced magnetic field $B_1$ is perpendicular to a static uniform magnetic field $B_0$ of the toroid cavity 104.

As shown in FIG. 1A, the capillary sample container 102 is coupled between a pump 120 at one end and a valve 122 at an opposite end outside the toroid cavity 104. A generally continuous column of sample material is provided within the capillary sample container 102 adjacent to the central conductor 106 within the toroid cavity 104.

Figure 4:
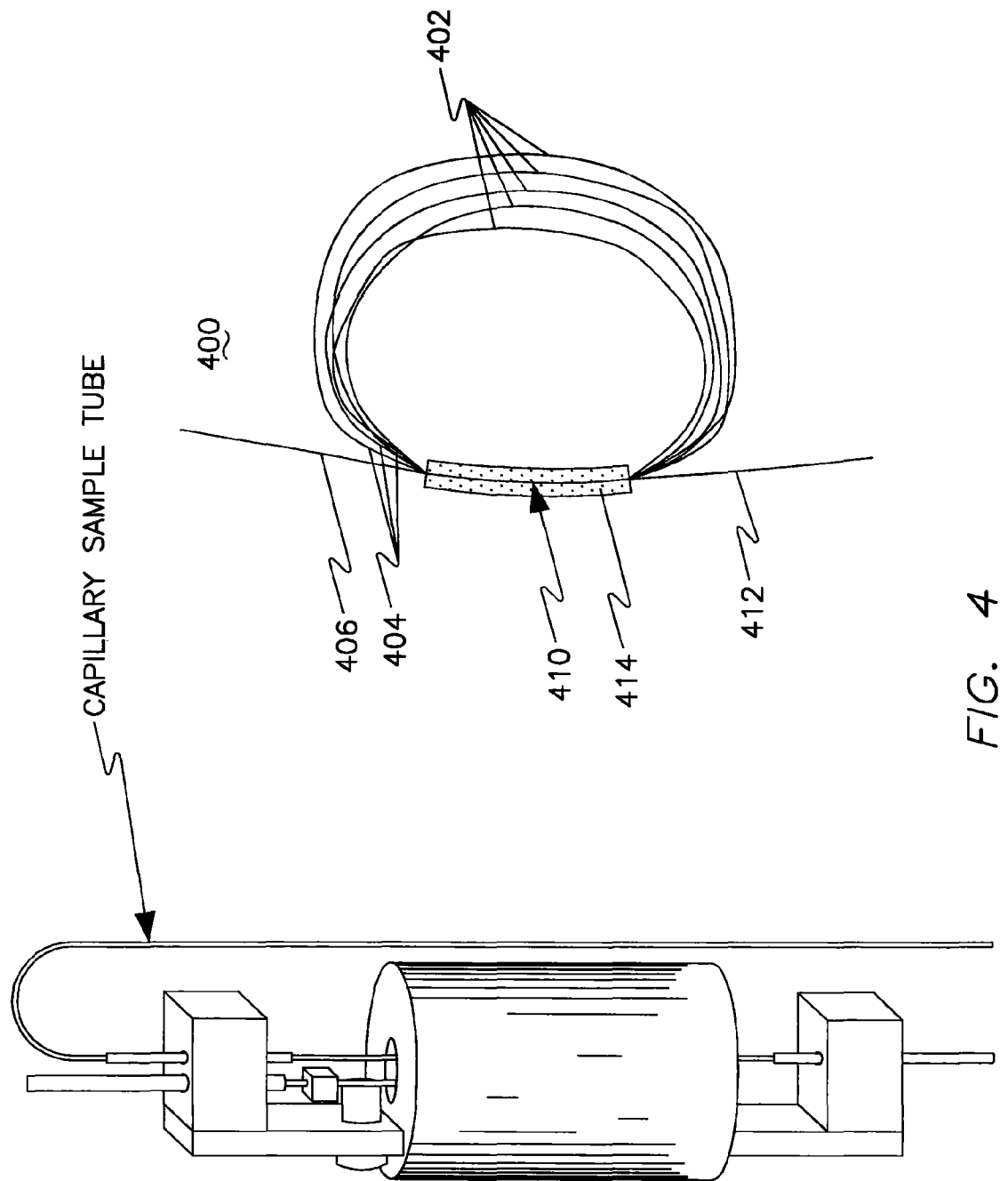
FIG. 4 illustrates a glass capillary tube including multiple loops for use with the high-pressure capillary TCD of FIG. 1A with a section of each loop adjacent to the central conductor of a preferred embodiment.

In accordance with features of the invention, the capillary sample container 102 advantageously is looped through the toroid cavity 104 multiple times, with a section of each capillary tube loop positioned adjacent to the central conductor 106, for example, as illustrated and described with respect to FIG. 4. The magnitude of the NMR signal increases in direct proportion to the number of loops of the capillary sample container 102.

Figure 1B:
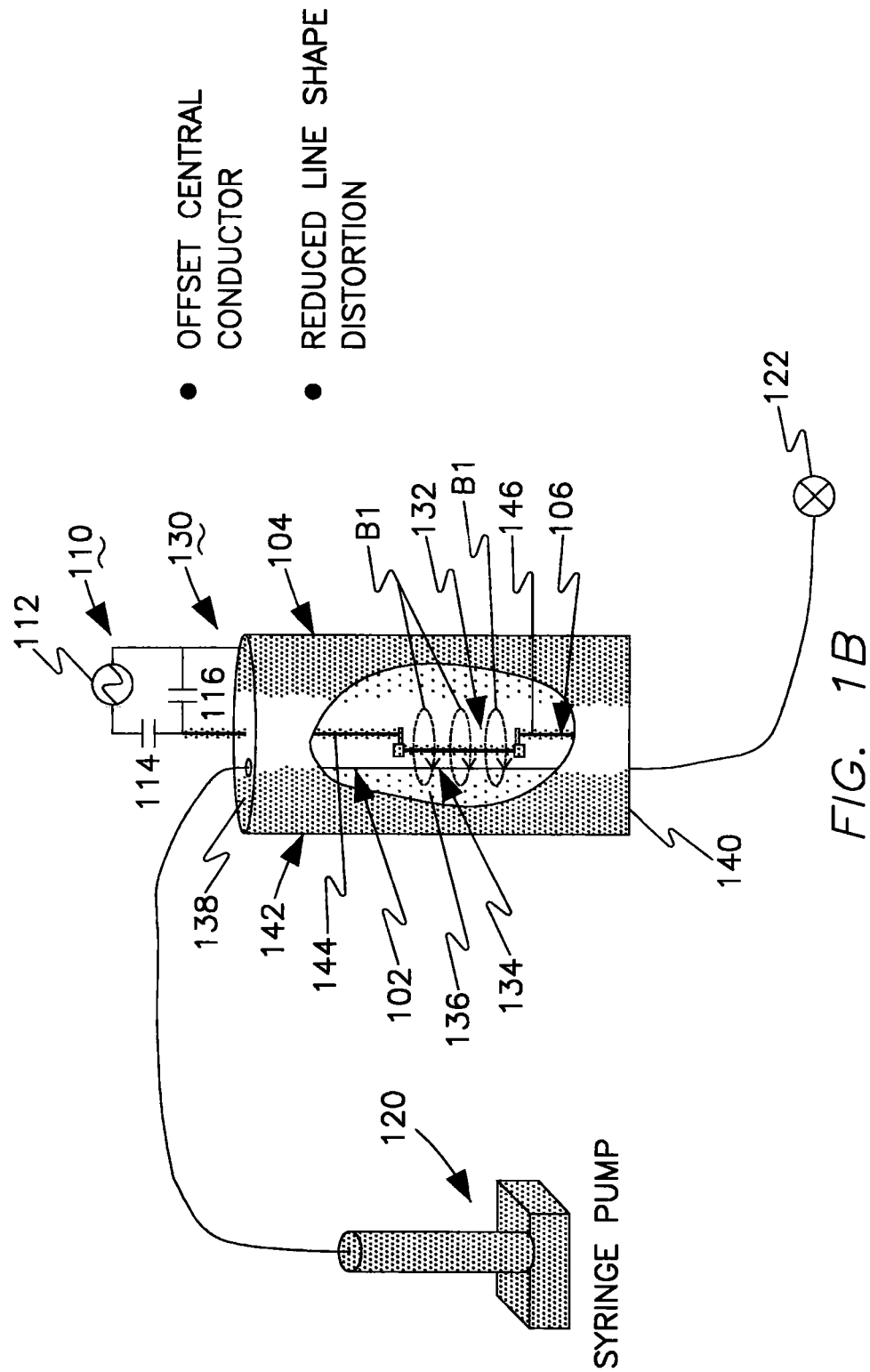
FIG. 1B illustrates a variation of the first embodiment of the high-pressure capillary TCD of FIG. 1A including an offset central conductor high-pressure capillary TCD of a preferred embodiment.

FIG. 1B illustrates a variation of the high-pressure capillary TCD 100 of FIG. 1A generally designated by the reference character 130 of a preferred embodiment. The same reference characters as used with respect to the high-pressure capillary TCD 100 of FIG. 1A are used for identical or substantially similar components in the high-pressure capillary TCD 130 of FIG. 1B. The elongated central conductor 106 includes a generally centrally located, laterally offset portion 132 within the toroid cavity 104. In the high-pressure capillary TCD 130, the capillary sample container 102 includes a section generally designated by 134.

With the capillary sample container 102 looped through the cavity multiple times, a section 134 of each capillary tube loop is positioned closely adjacent to the offset 132 of the central conductor 106. The purpose of the offset 132 of the central conductor 106 is to selectively interrogate only that section 134 of the capillary tube sample container 102 disposed within a generally central region 136 of the toroid cavity 104 having the most homogeneous field and that is spaced apart and generally far removed from a top 138 and a bottom 140 of the toroid cavity 104. The offset portion 132 is selectively positioned to cause maximum excitation of the sample in section 134 of the capillary tube sample container 102. The top 138 and bottom 140 of the toroid cavity 104 causes distortions in the static applied magnetic field $B_0$ in the cylindrical volume contained by the toroid cavity. The sample contained within the capillary tube sample container 102 in the region near the top 138 and the bottom 140 of the toroid cavity 104 is minimally excited due to the increased separation from the central conductor 106. The distortions are greatest near the top 138 and bottom 140 of the toroid cavity 104 due to the metal parts of the toroid cavity. A cavity cylinder wall 142 is oriented parallel to the magnetic field $B_0$ and thus does not cause distortions. In the center region 136 of the toroid cavity 104, the magnetic field distortions are minimal, and it is in that location that the sample should be placed for interrogation. Since the capillary sample container 102 is filled with a sample and spans the entire cavity length, the central conductor detector element should be generally sensitive only in the desired region where the static magnetic field is least distorted and this is accomplished by the offset 132 in the central conductor 106. A top section 144 and a bottom section 146 of the central conductor 106 are further removed from the capillary sample container 102 and thus detect those regions with poor sensitivity. Ideally, the top and bottom sections 144, 146 of the central conductor 106 would be shielded from interrogating the sample completely. This effect is accomplished in the embodiment shown in FIG. 1C.

Figure 1C:
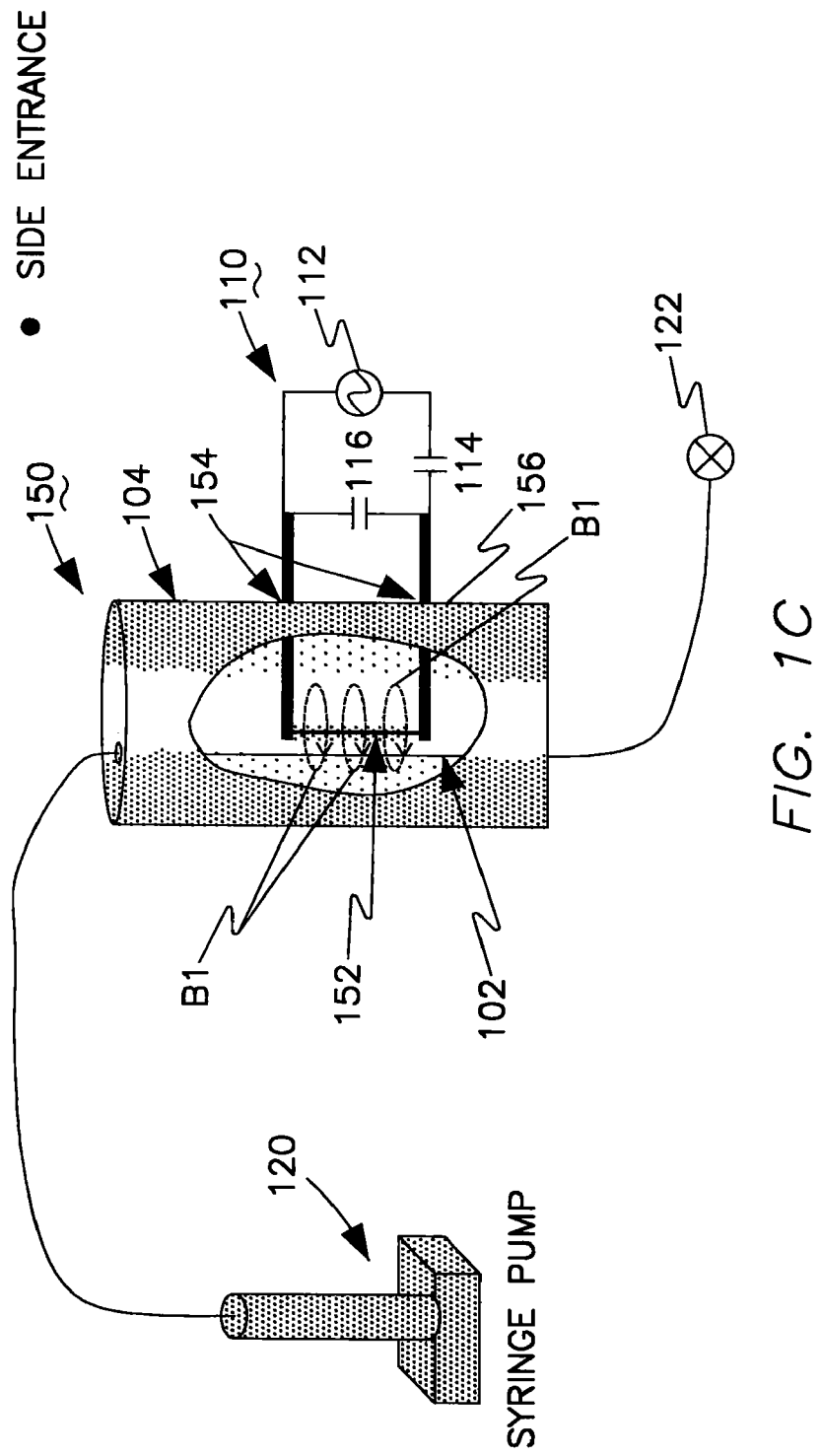
FIG. 1C illustrates another variation of the first embodiment of the high-pressure capillary TCD of FIG. 1A including a side entrance central conductor of a preferred embodiment.

FIG. 1C illustrates another high-pressure capillary TCD generally designated by the reference character 150 of a preferred embodiment having another offset central conductor arrangement. In the high-pressure capillary TCD 150, the same reference characters are used for identical or substantially similar components as used with respect to the high-pressure capillary TCD 100, 130 of FIGS. 1A and 1B, respectively. The high-pressure capillary TCD 150 includes an offset central conductor portion 152 by employing RF feedthroughs 154 at a side 156 of the toroid cavity 104 so that the top and bottom sections of the sample within the capillary sample container 102 are generally not interrogated.

Figure 2:
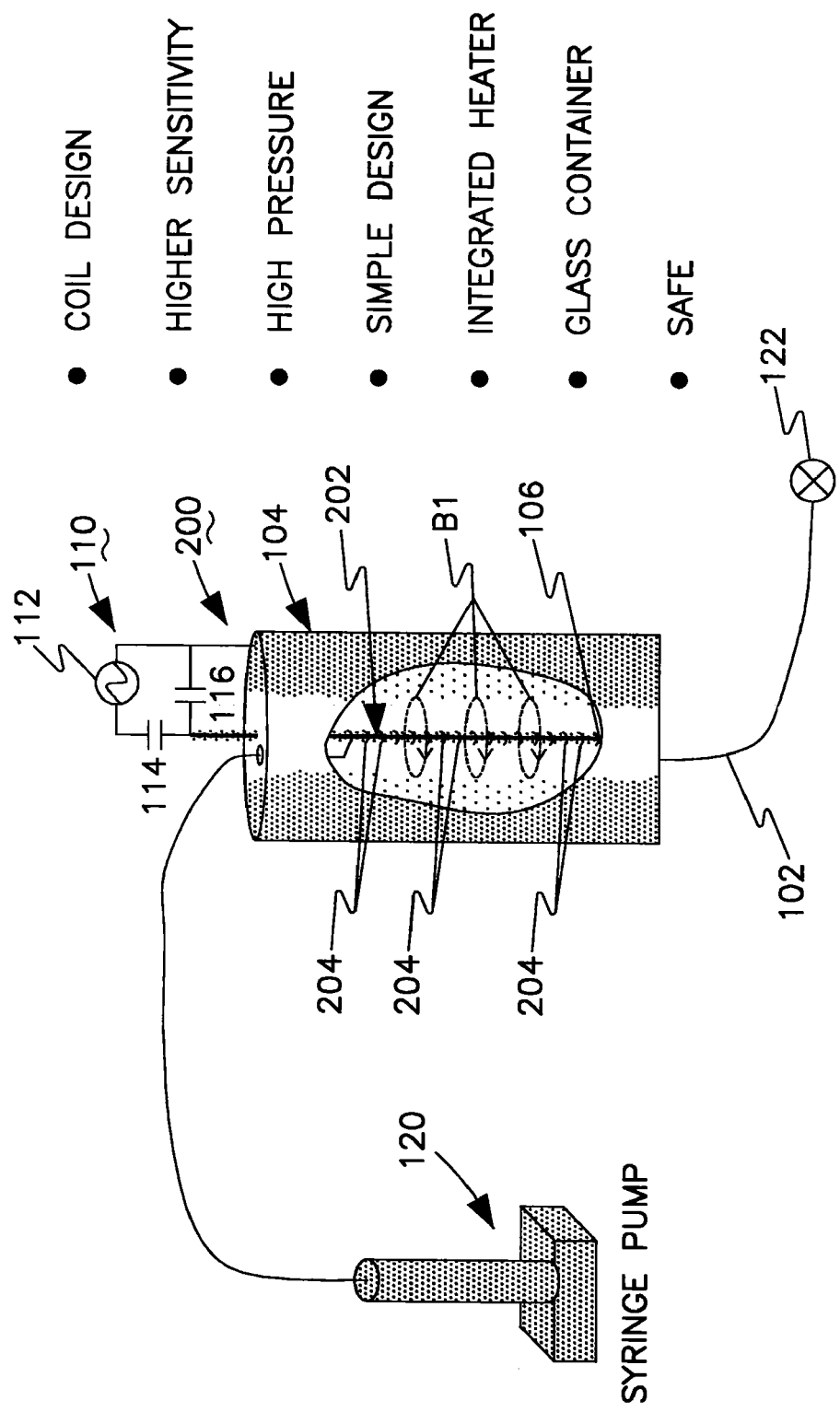
FIG. 2 illustrates a second embodiment of the high-pressure capillary TCD including a capillary sample tube wrapper around the central conductor of a preferred embodiment.

FIG. 2 illustrates another embodiment of a high-pressure capillary TCD generally designated by the reference character 200 of the preferred embodiment. In the high-pressure capillary TCD 200 the same reference characters are used for identical or substantially similar components as used with respect to the high-pressure capillary TCD 100 of FIG. 1A. The high-pressure capillary TCD 200 includes a capillary sample container 102 having a portion generally designated by 202 wound around the central conductor 106 within the toroid cavity 104. Wound portion 202 is a coil arrangement including a plurality of loops 204. The capillary sample container 102 may be looped around the central conductor 106 multiple times to increase the magnitude of the detected NMR signal. The magnitude of the NMR signal increases in direct proportion to the number of loops wrapped around the central conductor.

Figure 6:
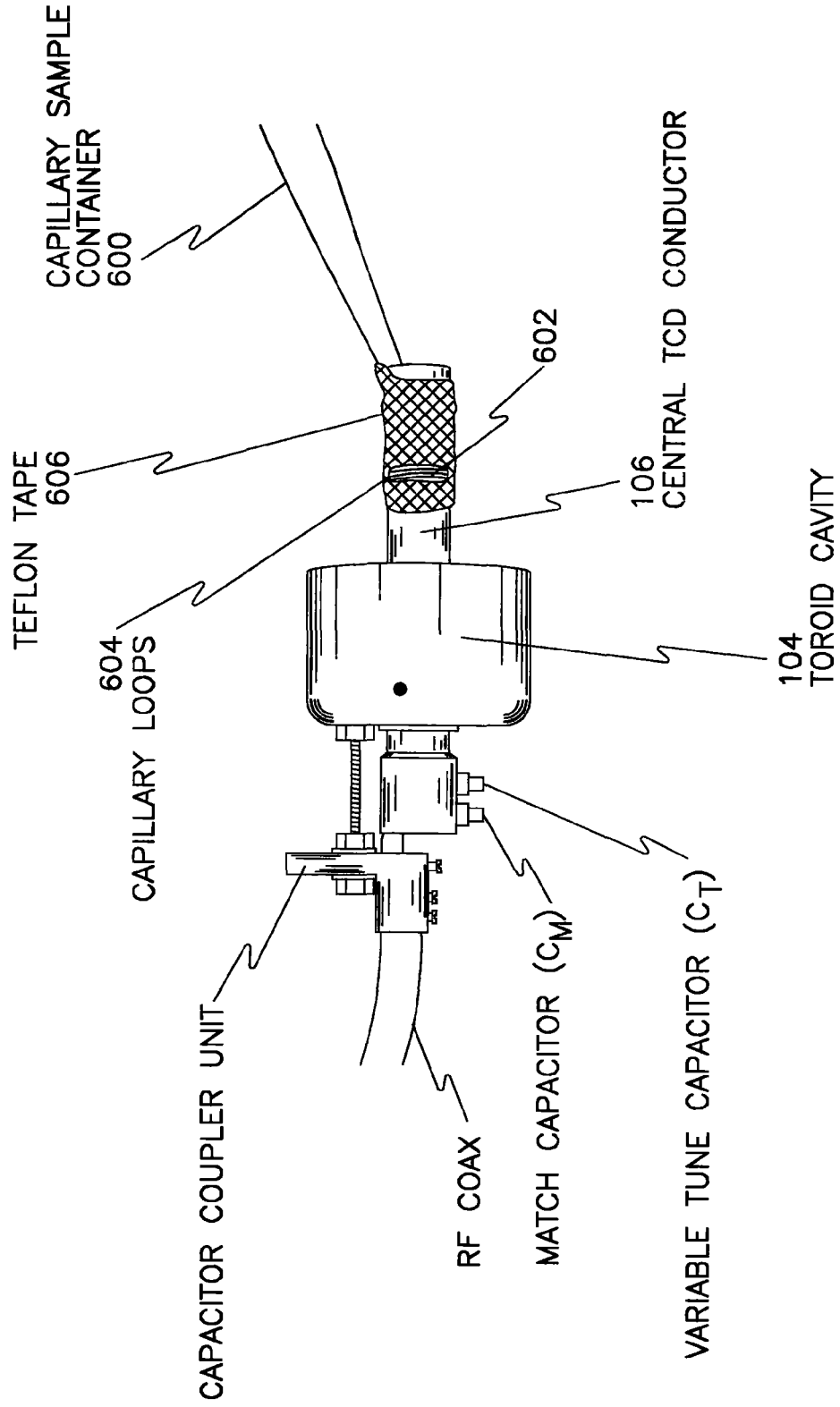
FIG. 6 illustrates an exemplary glass capillary tube wound around an enlarged diameter central conductor for use with the high-pressure capillary TCD of FIG. 2 of a preferred embodiment.

Another coil arrangement for looping the capillary sample container 102 around the central conductor 106 multiple times to increase the magnitude of the detected NMR signal is illustrated and described with respect to FIG. 6.

A prototype device was fabricated with a central conductor having a 0.5" outer diameter to reduce the stress on the glass capillary tube caused by high-curvature bends. A second prototype device was fabricated using a central conductor having a 0.25" outer diameter, and wrapped with Teflon capillary tubing.

Figure 3:
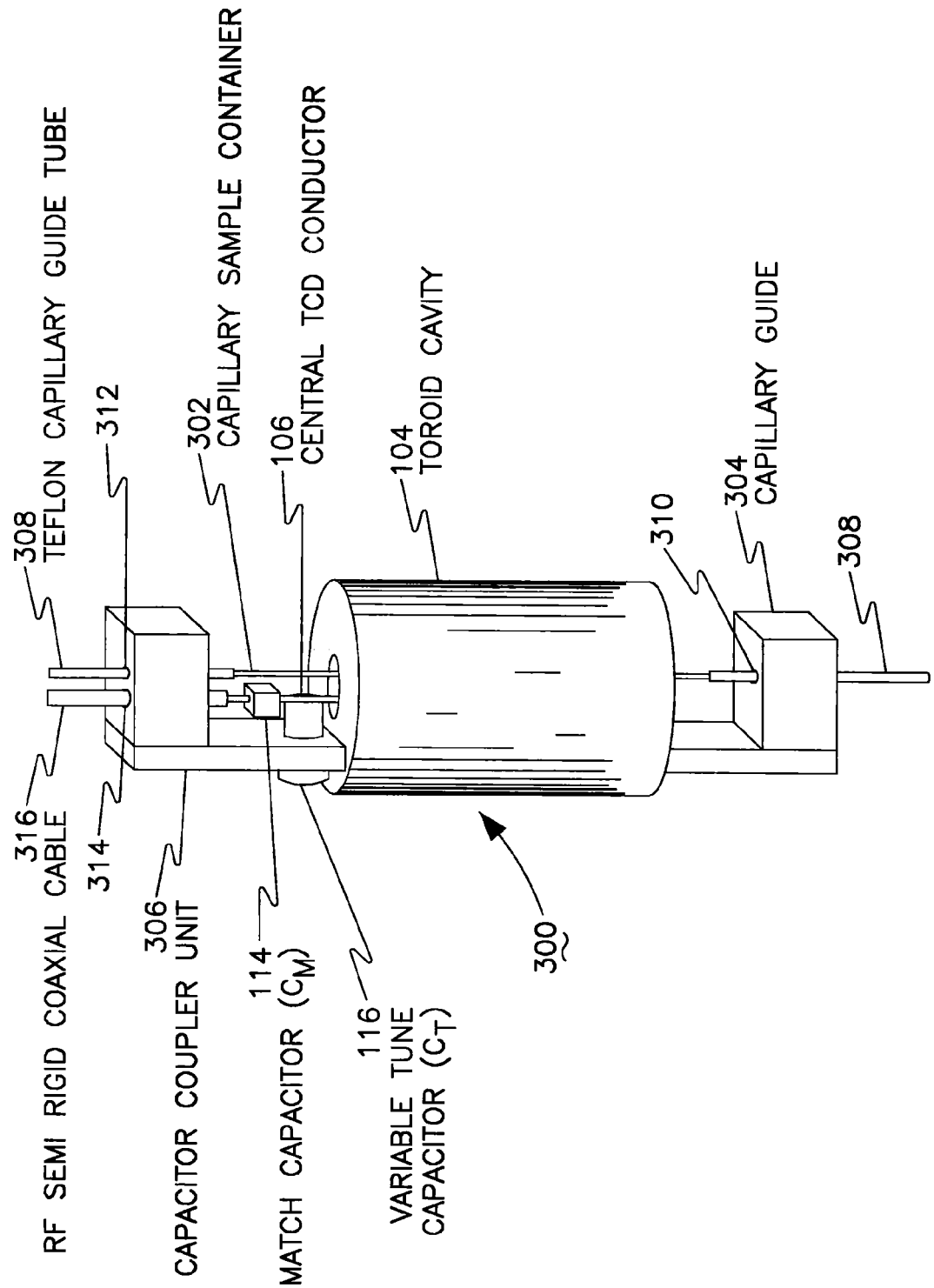
FIG. 3 illustrates a third embodiment of the high-pressure capillary TCD including a glass capillary tube adjacent to the central conductor of the TCD of a preferred embodiment.

FIG. 3 illustrates a high-pressure capillary TCD generally designated by the reference character 300. In the high-pressure capillary TCD 300, the same reference characters are used for identical or substantially similar components as used with respect to the high-pressure capillary TCD 100 of FIG. 1A. High-pressure capillary TCD 300 includes a flow-through capillary sample container 302 located within a toroid cavity 104 to subject a sample material flowing through the capillary sample container to static and RF magnetic fields and to enable NMR spectra to be recorded of the material in the capillary under a high temperature and high pressure environment of the TCD 300. The flow-through capillary sample container 302 is located proximate to a central conductor 106 extending along a predefined axis, such as a central axis of the toroid cavity 104.

The flow-through capillary sample container 302 is a single-pass glass capillary tube adjacent to the central conductor 106 of the TCD 300. The capillary tube 302 enters the TCD 104, for example, from the bottom of a vertical-bore superconducting magnet and exits from the top. A capillary guide 304 and a capacitor coupler unit 306 are disposed spaced apart from the bottom and top of the toroid cavity 104, respectively. The flow-through capillary sample container 302 is received through a respective Teflon capillary guide tube 308 and extends through a respective aligned opening 310, 312 within the capillary guide 304 and capacitor coupler unit 306, respectively. The capacitor coupler unit 306 includes an opening 314 receiving a RF semi rigid coaxial cable 316 connected to the central conductor 106.

FIG. 4 illustrates a glass capillary tube generally designated by the reference character 400 of a preferred embodiment. The glass capillary tube 400 includes a plurality of loops 402 demonstrating a return path 404 for each capillary tube loop 402 adjacent to an incoming path 406 for the capillary tube 400. A section generally designated by 410 of each loop 402 extends between the incoming path 406 and an outgoing path 412 of the glass capillary tube 400. A tube 414 contains each loop section 410 disposed proximate to the central conductor 106 within the toroid cavity 104. The glass capillary tube 400 advantageously is used with each of the high-pressure capillary TCDs 100, 130, 150 of FIGS. 1A, 1B, 1C, respectively, with the sections 410 of the multiple loops 402 adjacent to the central conductor 106 within the toroid cavity 104. The multiple loops 402 of capillary sample container 400 providing respective sections 410 proximate to the central conductor 106 to increase the magnitude of the detected NMR signal multiple times as compared to the single-pass flow-through capillary sample container 302 of FIG. 3. The magnitude of the NMR signal is directly proportional to the number of loops 402 and the corresponding number of sections 410 proximate to the central conductor 106.

Figure 5:
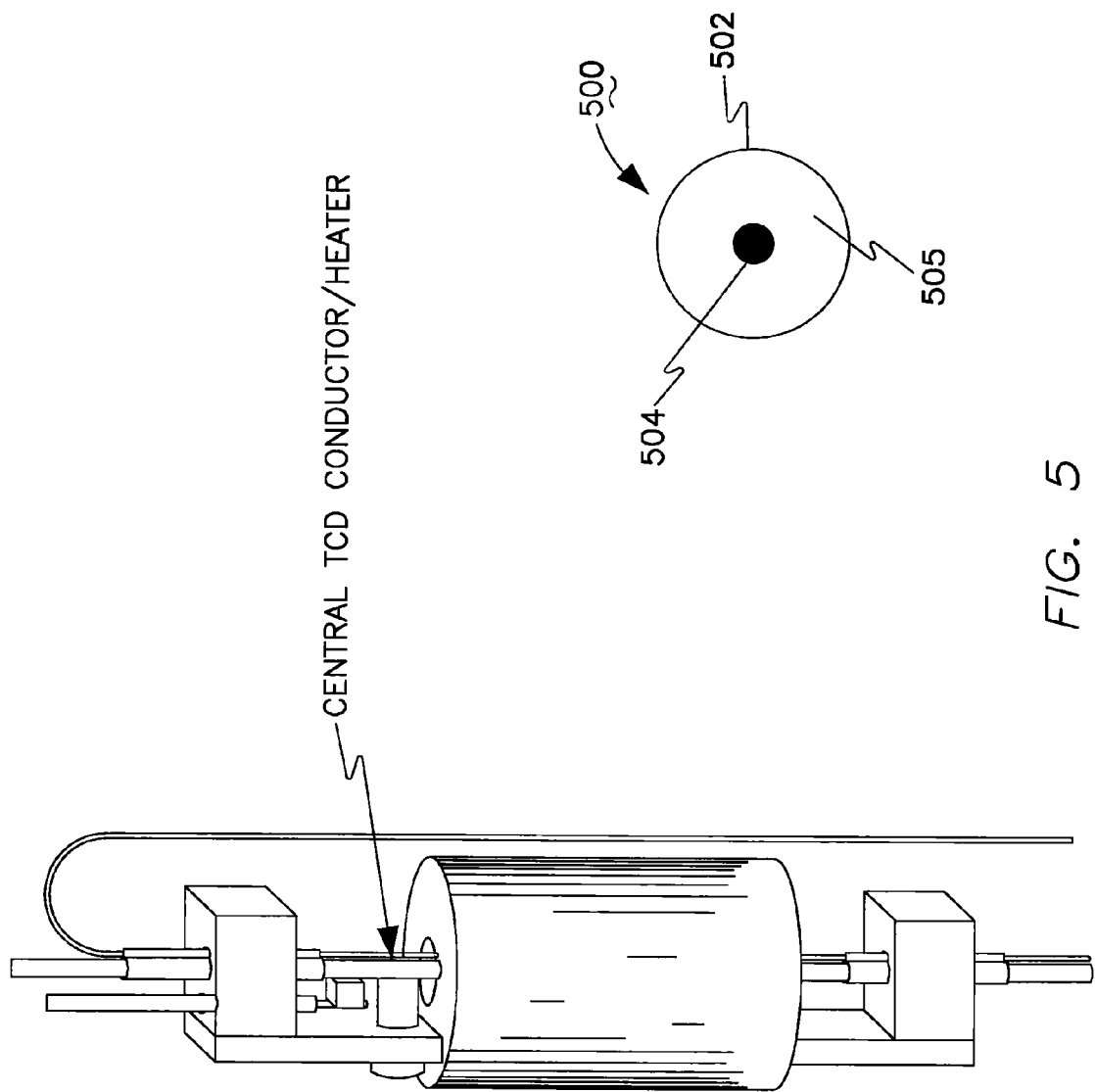
FIG. 5 illustrates a coaxial heater element contained within a hollow central conductor of a preferred embodiment.

FIG. 5 illustrates a heated central conductor arrangement generally designated by reference character 500 of the preferred embodiment. The heated central conductor arrangement 500 includes a hollow central conductor or electrically conductive tube 502 of the TCD. A coaxial heater element 504 is contained within the hollow central conductor 502, and can be employed to heat the sample. The central conductor tube 502 is formed of an electrically conductive material, such as, copper or beryllium copper (BeCu). The central conductor tube 502 is connected to an RF circuit, such as circuit 110 of FIG. 1A. The coaxial heater element 504 is formed of an electrically conductive material, such as, constantan or platinum. The coaxial heater element 504 is connected to a direct current power supply.

FIG. 6 is a photograph of the high-pressure capillary TCD 200 illustrating an exemplary glass capillary tube 600 wound around an enlarged diameter central conductor 106 of a preferred embodiment. The glass capillary tube 600 includes a coil arrangement 602 of a plurality of loops 604, each wrapped around the central conductor 106. A Teflon tape 606 holds the glass capillary tube coil arrangement 602 in place on the central conductor 106. The magnitude of the NMR signal is directly proportional to the number of loops 604 wrapped around the central conductor 106.

While the present invention has been described with reference to the details of the embodiments of the invention shown in the drawing, these details are not intended to limit the scope of the invention as claimed in the appended claims.

We claim:

1. A Toroid Cavity Detector (TCD) configured for implementing nuclear magnetic resonance (NMR) studies of chemical reactions under conditions of high pressures and temperatures comprising:
a toroid cavity containing an non-coiled elongated central conductor extending within said toroid cavity; said toroid cavity and non-coiled elongated central conductor for generating a radio frequency magnetic field for NMR analysis;
a flow-through capillary sample container having a segment located within a toroid cavity; at least a portion of said flow-through capillary sample container being positioned adjacent to said non-coiled elongated central conductor; and said flow-through capillary sample container having a sample material flowing only through and within said capillary sample container in order to enable NMR spectra to be recorded of said sample material under a temperature and high pressure condition.

2. A Toroid Cavity Detector (TCD) as recited in claim 1 wherein said flow-through capillary sample container includes a plurality of flow-though sample container loops, each loop having a section disposed proximate to said non-coiled elongated central conductor within said toroid cavity.

3. A Toroid Cavity Detector (TCD) as recited in claim 2 wherein said flow-through sample container includes a tube containing said sections of said plurality of flow-through sample container loops disposed proximate to said non-coiled elongated central conductor within said toroid cavity.

4. A Toroid Cavity Detector (TCD) as recited in claim 2 wherein said flow-through capillary sample container is formed from a material selected from the group consisting of glass, quartz, high performance polymers, metal oxides, and ceramics.

5. A Toroid Cavity Detector (TCD) as recited in claim 1 wherein said flow-through capillary sample container includes a plurality of flow-through sample container loops extend around said non-coiled elongated central conductor within said toroid cavity.

6. A Toroid Cavity Detector (TCD) as recited in claim 5 wherein said plurality of flow-through sample container loops extend around said non-coiled elongated central conductor within said toroid cavity includes a coil arrangement.

7. A Toroid Cavity Detector (TCD) as recited in claim 5 wherein said flow-through capillary sample container is formed from a material selected from the group consisting of glass, quartz, high performance polymers, metal oxides, and ceramics.

8. A Toroid Cavity Detector (TCD) as recited in claim 1 wherein said non-coiled elongated central conductor extending within said toroid cavity includes a hollow central electrically conductive tube.

9. A Toroid Cavity Detector (TCD) as recited in claim 8 wherein said non-coiled elongated central conductor extending within said toroid cavity includes a coaxial heater element contained within said hollow central electrically conductive tube.

10. A Toroid Cavity Detector (TCD) as recited in claim 9 wherein said hollow central electrically conductive tube is formed of an electrically conductive material selected from a group including copper and beryllium copper (BeCu).

11. A Toroid Cavity Detector (TCD) as recited in claim 9 wherein said coaxial heater element is formed of an electrically conductive material selected from a group including constantan.

12. A Toroid Cavity Detector (TCD) as recited in claim 1 wherein said non-coiled elongated central conductor extending within said toroid cavity includes a portion positioned closely adjacent to said flow-through capillary sample container; said portion of said central non-coiled elongated conductor disposed within a generally central region of said toroid cavity in order to selectively interrogate a predefined section of said flow-through capillary sample container.

13. A Toroid Cavity Detector (TCD) as recited in claim 12 wherein said non-coiled elongated central conductor portion is defined by an offset portion of said non-coiled elongated central conductor extending within said toroid cavity; said central non-coiled elongated central conductor extending between a top and a bottom of said toroid cavity.

14. A Toroid Cavity Detector (TCD) as recited in claim 12 wherein said non-coiled elongated central conductor portion is defined by an interior portion of said non-coiled elongated central conductor extending between a pair of feedthroughs providing a side entrance to said toroid cavity.

15. The toroid Cavity Detector (TCD) as recited in claim 1 wherein the sample is at a pressure of from about 5 atm to about 1500 atm.

16. The toroid Cavity Detector (TCD) as recited in claim 1 wherein the sample is at a temperature of from about 50° C. to about 500° C.

17. The toroid Cavity Detector (TCD) as recited in claim 1 wherein the sample is at a temperature of from about −200° C. to about 0° C.

18. The toroid Cavity Detector (TCD) as recited in claim 1 wherein the sample is at a temperature of from about 0° C. to about 50° C.

19. A Toroid Cavity Detector (TCD) configured for implementing nuclear magnetic resonance (NMR) studies of chemical reactions under conditions of high pressures and temperatures comprising:
   a toroid cavity containing a non-coiled elongated central conductor extending within said toroid cavity; said toroid cavity and said non-coiled elongated central conductor for generating a radio frequency magnetic field for NMR analysis;
   a flow-through capillary sample container having a segment located within a toroid cavity; said flow-through capillary sample container having a sample material flowing only through and within said capillary sample container in order to enable NMR spectra to be recorded of said sample material under the temperature and high pressure conditions of said toroid cavity;
   said flow-through capillary sample container including a plurality of flow-through sample container loops, each flow-through sample container loop including at least a portion positioned adjacent to said non-coiled elongated central conductor.

20. The toroid Cavity Detector (TCD) as recited in claim 19 wherein said plurality of flow-though sample container loops of said flow-through capillary sample container include a coil arrangement with each flow-through sample container loop extending around said non-coiled elongated central conductor.

21. The toroid Cavity Detector (TCD) as recited in claim 19 wherein said flow-through capillary sample container is formed from a material selected from the group consisting of glass, quartz, high performance polymers, metal oxides, and ceramics.

22. The toroid Cavity Detector (TCD) as recited in claim 19 wherein said non-coiled elongated central conductor extending within said toroid cavity includes a coaxial heater element contained within a hollow central electrically conductive tube.

23. The toroid Cavity Detector (TCD) as recited in claim 19 wherein said coaxial heater element is spaced apart from said hollow central electrically conductive tube.

24. The toroid Cavity Detector (TCD) as recited in claim 19 wherein said non-coiled elongated central conductor extending within said toroid cavity includes a portion positioned closely adjacent to said flow-through capillary sample container; said portion of said non-coiled elongated central conductor is disposed within a generally central region of said toroid cavity in order to selectively interrogate a predefined section of said flow-through capillary sample container.

* * * * *